(12) United States Patent
Ogawa et al.

(10) Patent No.: US 7,045,789 B2
(45) Date of Patent: May 16, 2006

(54) RADIATION DETECTION DEVICE FOR NUCLEAR MEDICINE DIAGNOSIS DEVICE AND DETECTING METHOD THEREFOR

(75) Inventors: Koichi Ogawa, Tokyo (JP); Takuzo Takayama, Tochigi (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 378 days.

(21) Appl. No.: 10/381,601

(22) PCT Filed: Oct. 1, 2001

(86) PCT No.: PCT/JP01/08656

§ 371 (c)(1),
(2), (4) Date: Apr. 3, 2003

(87) PCT Pub. No.: WO02/29438

PCT Pub. Date: Apr. 11, 2002

(65) Prior Publication Data

US 2004/0031926 A1    Feb. 19, 2004

(30) Foreign Application Priority Data

Oct. 4, 2000  (JP) ............................ 2000-304705

(51) Int. Cl.
*G01T 1/164*   (2006.01)
*G01T 1/24*    (2006.01)

(52) U.S. Cl. .............................. 250/363.03; 250/370.09

(58) Field of Classification Search ........... 250/363.03, 250/363.04, 363.02, 370.08, 363.07, 369, 250/370.09, 370.06
See application file for complete search history.

(56) References Cited

U.S. PATENT DOCUMENTS 5,525,803 A  *  6/1996  Watanabe et al. ........... 250/369
5,753,917 A  *  5/1998  Engdahl ..................... 250/367
5,818,050 A  * 10/1998  Dilmanian et al. ..... 250/363.09
6,175,116 B1 *  1/2001  Gagnon et al. ........ 250/363.03
6,285,028 B1 *  9/2001  Yamakawa ............. 250/370.09
6,423,971 B1 *  7/2002  Yamakawa ............. 250/363.03
6,621,084 B1 *  9/2003  Wainer et al. ......... 250/370.09
6,657,200 B1 * 12/2003  Nygard et al. ......... 250/370.09
6,858,847 B1 *  2/2005  Macciocchi ............. 250/363.03
2004/0124361 A1* 7/2004  Yamakawa ............. 250/370.09

FOREIGN PATENT DOCUMENTS

| JP | 11-304926 | 11/1999 |
| JP | 11-337647 | 12/1999 |
| WO | 93/09447 | 5/1993 |

* cited by examiner

*Primary Examiner*—Albert Gagliardi
(74) *Attorney, Agent, or Firm*—Oblon, Spivak, McClelland, Maier & Neustadt, P.C.

(57) ABSTRACT

In case of performing so-called "PET acquisition", a nuclear medical diagnosis apparatus according to the present invention does not set only gamma rays which imparted predetermined energy values (for example, energy values of and above a Compton edge), as subjects for coincidental counting acquisition (coincidence acquisition), but it discriminates also further gamma rays which caused a photoelectric effect after having undergone Compton scattering once in a radiation detection unit, so as to set them as subjects for the coincidental counting acquisition. Concretely, if the added value of energy values observed in two detection elements is "near 511 keV", the existence of the further gamma ray is presumed, and the acquisition thereof is possible. Besides, that one of the two detection elements as to which energy near the Compton edge is observed can be specified as the incident position of the gamma ray on the radiation detection unit.

2 Claims, 9 Drawing Sheets

RADIATION DETECTION DEVICE FOR NUCLEAR MEDICINE DIAGNOSIS DEVICE AND DETECTING METHOD THEREFOR

CROSS-REFERENCE TO RELATED APPLICATIONS

This is a Continuation Application of PCT Application No. PCT/JP01/08656, filed Oct. 1, 2001, which was not published under PCT Article 21(2) in English.

This application is based upon and claims the benefit of priority from the prior Japanese Patent Application No. 2000-304705, filed Oct. 4, 2000, the entire contents of which are incorporated herein by reference.

BACKGROUND OF THE INVENTION

1. Field of the Invention

The present invention relates to a radiation detection device and a radiation detection method in a nuclear medical diagnosis apparatus.

2. Description of the Related Art

Heretofore, there has been provided a nuclear medical diagnosis apparatus wherein a subject is dosed with a drug which is labeled with a radioisotope (hereinbelow, sometimes abbreviated to "RI"), and the state of an RI distribution in the body of the subject is imaged on the basis of a result which is obtained by sensing and measuring gamma rays emitted from the RI, by means of a radiation detection unit. In particular, an SPECT (Single Photon Emission Computed Tomography) apparatus has been extensively known as an apparatus or means for radiographing the above image as a three-dimensional distribution image (tomogram). Owing to such an image, the user of the apparatus or an operator can confirm the situation of the interior of the body of the subject for example, a morbid part, a blood stream or a fatty-acid metabolic rate) without resorting to surgical means.

Besides, there has been known a PET (Positron Emission Tomography) apparatus wherein a plurality of such radiation detection units are included, and a positron emitting nuclide is utilized as the radioisotope, so as to image a pair of gamma rays which are emitted in directions of 180 degrees at the annihilation of a positron by combining with an electron, and which are coincidentally detected by the plurality of radiation detection units (as a coincidental counting measurement, or the coincidence acquisition of the gamma rays). Incidentally, there has also been known a so-called "combined SPECT/PET apparatus" which is capable of implementing both PET and SPECT by an identical system.

By the way, in the above apparatus, a suitable energy range (or energy window) is usually set, whereby only gamma rays having energy levels within the range are acquired. Here, the suitable energy range is set as, for example, "energy of and above a Compton edge", and all the gamma rays corresponding thereto are acquired to form the basis of the imaging. Thus, gamma rays having given rise to a photoelectric effect can be utilized as principal basic data on the occasion of the imaging.

Herein, the radiation detection unit fundamentally has the function of receiving the incidence of the gamma rays, and converting the gamma rays into electric signals (easy of handling) while mirroring the incident positions and energy levels thereof. The practicable aspects of the radiation detection unit are of two broad sorts called a "scintillation camera" and a "semiconductor detector".

The scintillation camera is chiefly constituted by a scintillator (made of, for example, an NaI crystal, BGO, or LSO) and a photo multiplier tube (PMT). According to this, the gamma rays incident on the scintillator are converted into light signals, which are converted into the electric signals by the photo multiplier tube. On the other hand, the semiconductor detector is so constructed that a plurality of semiconductor detection elements (of, for example, CdTe or CdZnTe) in which the incidence of the gamma rays contributes to the creation of charges (that is, the generation of the electric signals) are arrayed, for example, planarly (in the shape of a matrix) and discretely.

Meanwhile, in the nuclear medical diagnosis apparatus as explained above, a theme to be stated below is generally existent. It is to enhance the efficiency of the gamma-ray acquisition in the radiation detection unit. The reason therefor is that, since the result of the gamma-ray acquisition forms the basis of the imaging as stated above, usually a higher acquisition efficiency is more favorable in order to guarantee the image quality and preciseness of the imaging.

In this regard, in a case where the scintillation camera is utilized as the radiation detection unit and where its scintillator is made of the BGO, LSO or the like, stopping power for the gamma rays is comparatively high. Therefore, most of the incident gamma rays give rise to the photoelectric effect within the scintillator, and the gamma rays can be acquired without being wasted (that is, all the energy can be imparted into the scintillator), so that the problem of the acquisition efficiency can be said less serious.

However, in a case where the semiconductor detector is used, the stopping power is comparatively lower than in the scintillator, and many of the incident gamma rays undergo transmission etc. without causing interactions with the detection elements. Besides, although it is unreasonable to go to the extent of saying that the gamma rays are transmitted through the detection elements without imparting any energy thereto, it can be said by way of example that the gamma rays are transmitted after causing Compton scattering, or that they give rise to the photoelectric effect after having caused the Compton scattering. That is, in the case of utilizing the semiconductor detector, it is usually difficult to impart the energy of all the gamma rays to the detection elements, and the acquisition efficiency for the gamma rays accordingly lowers. Therefore, the quality of the image of the gamma rays has also been affected. Incidentally, when the thickness of the semiconductor detection elements is enlarged in order to heighten the stopping power with the intention of eliminating such a drawback, the Compton scattering occurs a plurality of times, and it becomes impossible to specify the incident positions of the gamma rays.

Besides, even with the scintillation camera, in a case where the scintillator is made of NaI or the like, the stopping power is usually low, and hence, there has been the possibility that the same problem as stated above will be similarly posed.

By the way, such a fact becomes more problematic in a case where the gamma rays are high in energy. Besides, in such a case, an attempt to heighten an acquisition efficiency for the high-energy gamma rays is recognized as the general theme irrespective of the sorts of the scintillation camera and the semiconductor detector as stated at the beginning of this section.

The present invention has been made in view of the above circumstances, and has for its object to provide, in a radiation detection unit, a radiation detection device for a nuclear medical diagnosis apparatus as is capable of enhancing an acquisition efficiency for gamma rays of high energy.

BRIEF SUMMARY OF THE INVENTION

The present invention has adopted the following means in order to accomplish the object:

A radiation detection device for a nuclear medical diagnosis apparatus as defined in claim 1 is a radiation detection device for a nuclear medical diagnosis apparatus having radiation detection means for detecting gamma rays emitted from a radioisotope in a body of a subject, by a plurality of radiation detection cells, characterized in that the radiation detection means is made radiation detection means for discriminating and acquiring gamma rays which imparted predetermined energy, and for discriminating and acquiring also gamma rays which caused a photoelectric effect after having undergone Compton scattering once within the radiation detection means.

Besides, a radiation detection device for a nuclear medical diagnosis apparatus as defined in claim 2 is a radiation detection device for a nuclear medical diagnosis apparatus having at least two radiation detection means for detecting gamma rays emitted from a radioisotope in a body of a subject, by a plurality of radiation detection cells, characterized in that, in a case where the gamma rays are gamma rays emitted in directions of 180 degrees at combination of a positron and an electron, and where coincidental counting acquisition is performed for the gamma rays coincidentally detected in two of the radiation detection means, the radiation detection means is made radiation detection means for discriminating gamma rays which imparted predetermined energy, so as to submit them to the coincidental counting acquisition, and for discriminating also gamma rays which caused a photoelectric effect after having undergone Compton scattering once within the radiation detection means, so as to submit them to the coincidental counting acquisition.

Further, a radiation detection device for a nuclear medical diagnosis apparatus as defined in claim 3 is the device as defined in claim 1 or 2, characterized in that the radiation detection means is a semiconductor detector.

In addition, radiation detection devices for a nuclear medical diagnosis apparatus as defined in claims 4 through 7 are respectively the devices as defined in claim 2, characterized in that, in a case where the Compton scattering and the photoelectric effect are respectively caused in adjacent ones of the radiation detection cells by the gamma ray, the gamma ray is set as a subject for the coincidental counting acquisition (claim 4); characterized in that energy quantities imparted to the radiation detection cells through the Compton scattering and the photoelectric effect are confirmed, thereby to specify an incident position of the gamma ray on the radiation detection unit (claim 5); characterized in that the radiation detection cells are divided into a plurality of groups, and that the discrimination is performed every group (claim 6); and characterized in that, in the coincidental counting acquisition of the gamma ray which underwent the Compton scattering once within the radiation detection means, the radiation detection cell as to which energy of the gamma ray falls within a range of 166 keV–300 keV is regarded as an incident position of the gamma ray (claim 7).

Besides, a radiation detection device for a nuclear medical diagnosis apparatus as defined in claim 8 is a radiation detection device for a nuclear medical diagnosis apparatus having radiation detection means for detecting gamma rays emitted from a radioisotope in a body of a subject, by a plurality of radiation detection cells, characterized by comprising a coincidentality decision portion which selects two gamma rays coincidentally detected by two of the radiation detection cells, and an added-energy discrimination portion which discriminates the two gamma rays in a case where an added value of energy values concerning the two gamma rays is equal to a predetermined value.

Further, claims 9–16 feature radiation detection methods respectively characterized by steps which are achieved by the constructions corresponding to the preceding claims 1–8 in succession.

DETAILED DESCRIPTION OF THE INVENTION

Figure 1:
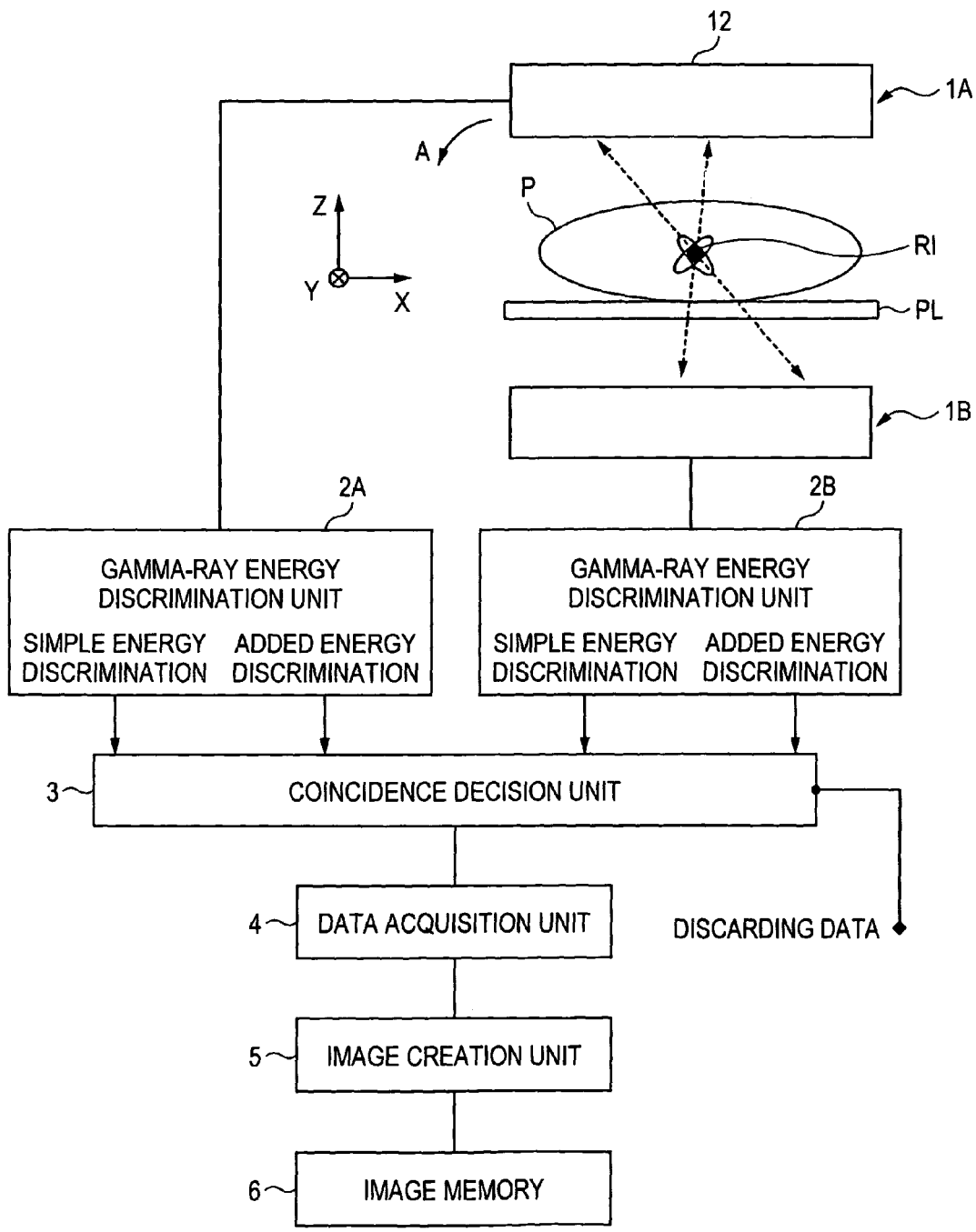
FIG. 1 is an outline diagram showing an example of construction of a radiation detection device for a nuclear medical diagnosis apparatus (hereinbelow, simply termed "nuclear medical diagnosis apparatus") according to an embodiment of the present invention.

Now, the first embodiment of the present invention will be described with reference to the drawings. FIG. 1 is an outline diagram showing an example of construction of a nuclear medical diagnosis apparatus according to this embodiment. Referring to FIG. 1, the nuclear medical diagnosis apparatus is constructed of radiation detection units (radiation detection means) 1, gamma-ray energy discrimination units 2, a coincidence decision unit 3, a data acquisition unit 4, an image creation unit 5 and an image memory 6.

Each radiation detection unit 1 has a general external view in a flat shape, and it is configured of a plurality of semiconductor detection elements 12 (termed "radiation detection cells" in the present invention, and hereinbelow called "detection elements") which are arrayed discretely and in the shape of a matrix within an XY-plane indicated in FIG. 1.

Besides, as shown in FIG. 1, the radiation detection units 1 in this embodiment are disposed in the number of two (refer to symbols 1A and 1B in the figure, both units having the same constructions) so that the respective units may oppose to each other around a subject P who is lying on the tabletop PL of a diagnostic table. PET acquisition to be stated later is permitted by utilizing the two radiation detection units 1A and 1B. Further, the radiation detection units 1A and 1B are entirely supported by a turning arm not shown, and they can rotate round the subject P as indicated by an arrow A in the figure.

The detection elements 12 receive gamma rays emitted from a radioisotope with which the subject P is dosed, and they directly convert the gamma rays into electric signals. Each of the electric signals contains position information and energy information respectively representing which position in the radiation detection unit 1A or 1B the originating gamma ray was sensed at (in other words, "which" detection element 12 it was sensed at), and how much energy the corresponding gamma ray has.

More concretely, a compound semiconductor; cadmium telluride (CdTe), for example, can be used for the detection element 12. Besides, the size of the detection element 12 can be set at, for example, 1.6 mm×1.6 mm per area on which the gamma ray is incident. By the way, in the present invention, a compound semiconductor CdZnTe may well be employed for the detection element 12. Besides, in order to derive the electric signal, the detection element 12 is additionally provided with an electrode not shown. The electrode has, for example, a Schottky structure which is formed of platinum and indium, and the platinum side thereof is used as an electrode for applying a high voltage, while the indium side thereof is used as an electrode for deriving the signal. Further, an insulating sheet or the like, not shown, is provided among the plurality of detection elements 12 disposed. In addition, the detection elements 12 are respectively furnished with charge amplifiers and waveshapers (neither of which is shown), through which the above electric signals are passed and outputted.

According to such a semiconductor detector, it is permitted to directly the electric signals from the gamma rays, unlike in the use of a scintillator. Moreover, the formation of the detection elements 12 is especially adapted to be easily made smaller in size (that is, the elements can be packaged more highly), so that the essential resolution, namely, so-called "intrinsic resolution" of the elements can be heightened.

Figure 2:
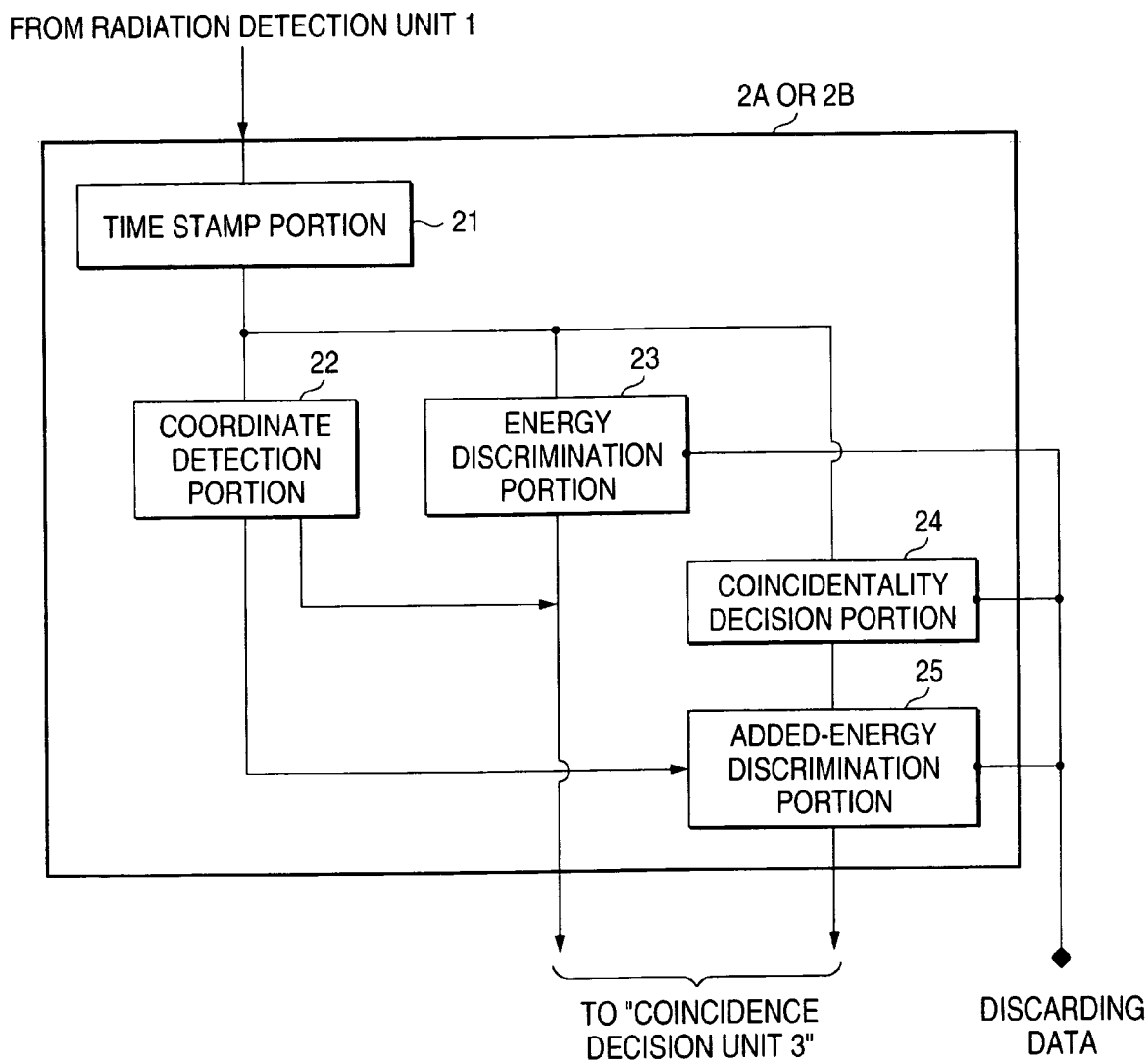
FIG. 2 is an outline diagram showing an example of construction of a gamma-ray energy discrimination unit shown in FIG. 1.

Meanwhile, referring to FIG. 1, the gamma ray energy discrimination units 2 are disposed in two sets (A and B) in correspondence with the fact that the two radiation detection units 1 are disposed as stated above. Besides, as shown in FIG. 2, the practicable construction of each of the gamma-ray energy discrimination units 2A and 2B is constituted by a time stamp portion 21, a coordinate detection portion 22, an energy discrimination portion 23, and a coincidentality decision portion 24 as well as an added energy discrimination portion 25. Two signals (simple energy discrimination and added energy discrimination) issued from each of the gamma-ray energy discrimination units 2A and 2B shown in FIG. 1 are respectively obtained by passing through the energy discrimination portion 23 and through the coincidentality decision portion 24 as well as the added-energy discrimination portion 25.

Referring to FIG. 2, the time stamp portion 21 stamps "when" the electric signal outputted from the radiation detection unit 1A or 1B was sensed on the corresponding radiation detection unit 1A or 1B (=a sensing time). Besides, the coordinate detection portion 22 specifies "which" detection element 12 of the radiation detection unit 1A or 1B the originating gamma ray of the electric signal was incident on, that is, it extracts position information.

The energy discrimination portion 23 decides whether or not energy information contained in the electric signal falls within a predetermined energy range. When the energy information is judged to fall within the range, the portion 23 issues an energy signal proportional to the energy of the gamma ray (a signal based on simple energy discrimination, as to which refer to FIG. 1), and when not, it does not issue any signal. Incidentally, the "energy range" stated here can be set by the user of the apparatus in such a way, for example, that a minimum value and a maximum value, or a minimum value (or a maximum value) and a predetermined width having the minimum value (or the maximum value) as one end are designated as to energy values. Besides, a plurality of such energy ranges can be set, and concretely, "energy of and above a Compton edge" or the like can be set as will be stated later.

Besides, in a case where the electric signals outputted from any two detection elements 12 in either of the radiation detection units 1A and 1B are recognized by the coincidentality decision portion 24 as having been "coincidentally" outputted (=in a case where gamma rays are recognized as having been coincidentally detected in the two detection elements 12), the added-energy discrimination portion 25 selects the two electric signals and adds up energy information items relevant to the two electric signals. When the sum of the addition is equal to a predetermined energy value (predetermined value), the portion 25 issues an energy signal proportional to the sum energy of the two gamma rays (a signal based on added energy discrimination, as to which refer to FIG. 1), and when not, it does not issue any signal.

Incidentally, the operation of the added-energy discrimination portion 25 will be stated in detail later. Besides, data passed through neither of the energy discrimination portion 23 and the added-energy discrimination portion 25 is discarded as shown in FIG. 2.

Referring back to FIG. 1, the coincidence decision unit 3 selects from the individual signals passed through the gamma-ray energy discrimination units 2A and 2B, ones whose sensing times stamped by the time stamp portion 21 are "coincidental" in the respective radiation detection units 1A and 1B, and it sends the selected data to the data acquisition unit 4. Incidentally, "coincidental" stated here corresponds to, for example, a case where the differences of the sensing times are within "10 ns" or so. The data acquisition unit 4 accumulates the sent data as gamma-ray data at any time. That is, in this embodiment, by passing the signals through the time stamp portion 21 and the coincidence decision unit 3, so-called "coincidence acquisition" (coincidental counting acquisition) is performed concerning the gamma rays sensed by the two sets of radiation detection units 1A and 1B. Incidentally, the signals which are not recognized as being coincidental are discarded as shown in FIG. 1.

The image creation unit 5 creates a planar image concerning an RI distribution within the subject P or reconstructs a tomogram on the basis of the gamma-ray data accumulated in the data acquisition unit 4, and the image memory 6 stores the created planar image or reconstructed tomogram therein. Incidentally, although not shown, an image display unit or the like is connected after the image memory 6 so as to display the image stored in the image memory 6.

The operation and advantages of the nuclear medical diagnosis apparatus of the above construction will be described below. Incidentally, the present invention features in the case of performing the PET acquisition, that, not only an image is formed on the basis of gamma rays having caused only a photoelectric effect, as usual, but also the data of gamma rays causing the photoelectric effect after having undergone Compton scattering once, among the gamma rays incident on the radiation detection units 1A and 1B, are utilized for imaging. Therefore, this point will be chiefly explained below.

Figure 3:
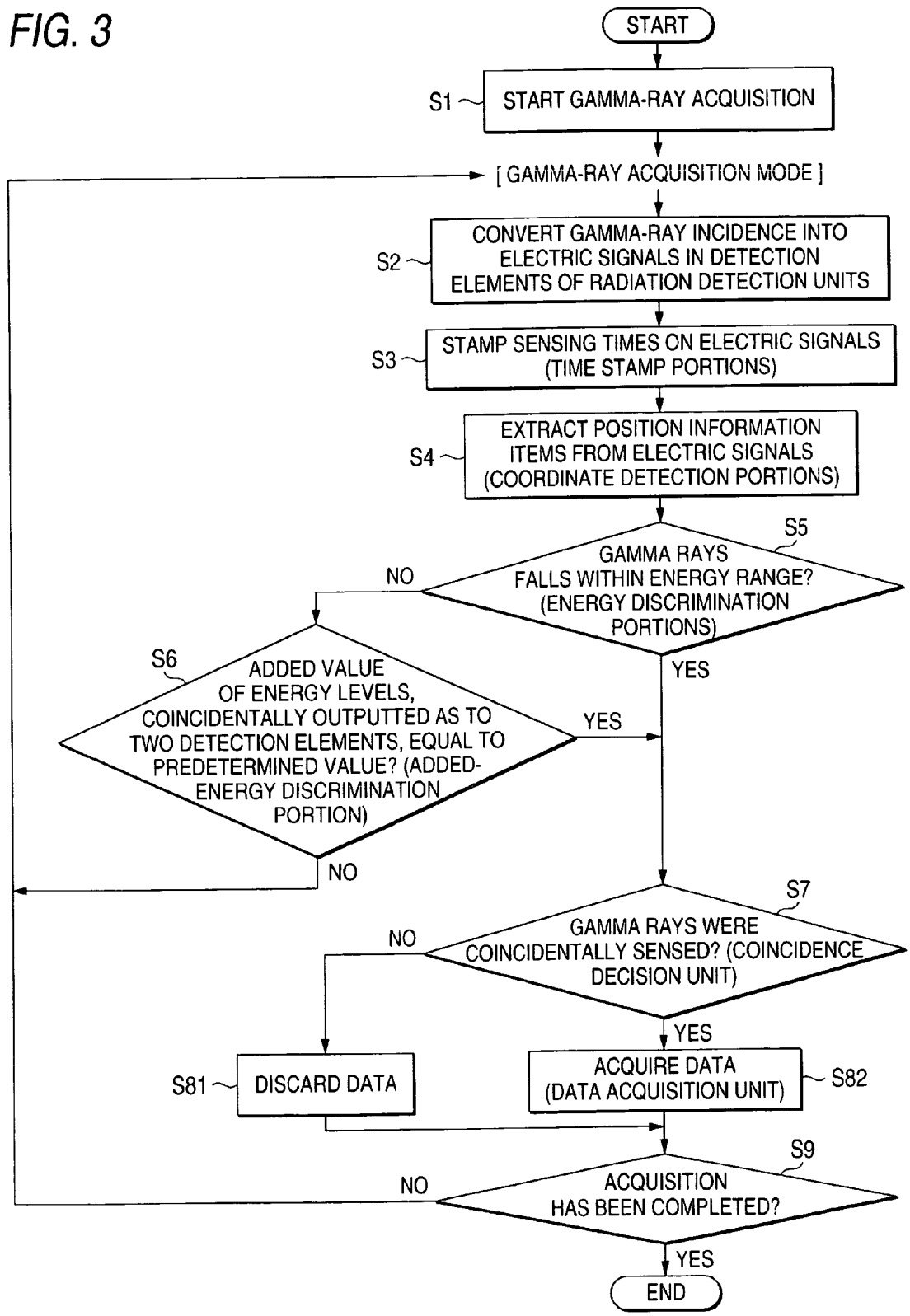
FIG. 3 is a flow chart showing the flow of the processing of gamma-ray acquisition in this embodiment.

First, as indicated at a step S1 in FIG. 3, the acquisition of gamma rays emitted from a radioisotope RI being a positron nuclide (for example, $^{11}$C or $^{13}$N), with which the subject P has been dosed, is started (=the user of the apparatus gives an acquisition start command) to enter a gamma-ray acquisition mode. The gamma rays are pairs of gamma rays which are emitted in the exact opposite directions (in directions of 180 degrees) to each other when a positron and an electron combine to annihilate (refer to broken lines which stretch from the radioisotope RI within the subject P in FIG. 1). Owing to the gamma-ray emission, three sorts of interactions; the photoelectric effect, the Compton effect and electron pair generation occur between the interiors of the radiation detection units 1 or the detection elements 12 thereof and the corresponding gamma rays.

Incidentally, as a premise for starting the gamma-ray acquisition stated now, the user of the apparatus can set the range of gamma-ray energy levels to-be-acquired (or an energy window), a time period for the acquisition, the number of counts for the acquisition, etc. Also, description will be developed below about a case where "energy of and above a Compton edge" is set as the energy range, namely, a range for the acquisition in the energy discrimination portion 23.

Figure 4:
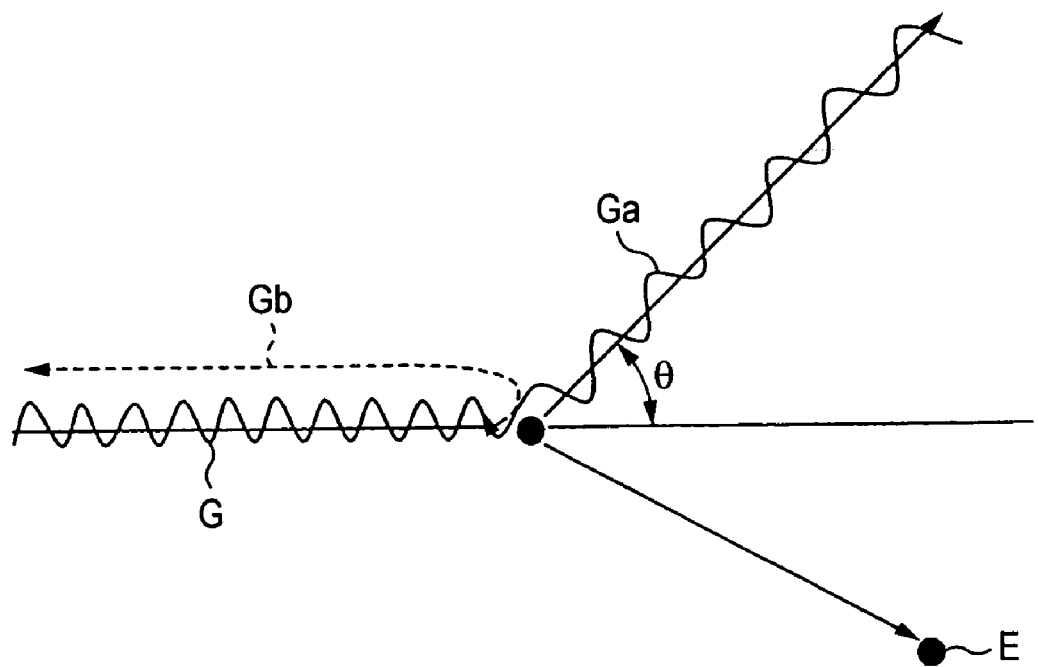
FIG. 4 is an explanatory diagram for explaining the phenomenon of Compton scattering.

By the way, the "Compton edge" concretely has a significance as stated below. First, the "Compton effect" is the phenomenon that, as shown in FIG. 4, an electron E in the detection element 12 and an incident gamma ray G come into elastic collision, whereby the electron E is emitted, while the gamma ray G is scattered (at Gs in the figure). On this occasion, energy Ee is imparted to the electron E by the gamma ray G. That is, the electric signal to be detected is proportional to the energy Ee. In this case, the momentum and energy of a system shown in the figure are conserved as is well known, the energy can be expressed by introducing a scattering angle θ, as follows:

$$Ee=E/(1+m_e c^2/E(1-\cos \theta)) \quad (1)$$

Here, $m_e$ denotes the rest mass of the electron E, and c denotes the velocity of light.

In this regard, in a case where the scattering angle θ is 180 degrees in the above equation (1), that is, where the gamma ray G scatters backward as indicated by symbol Gb in FIG. 4, cos θ=−1 holds, and the energy Ee exhibits a maximum value Ee max. Besides, the maximum energy Ee max is generally called the "Compton edge", and it becomes as follows from Eq. (1):

$$E_e \max=E/(1+m_e c^2/2E) \quad (2)$$

Owing to the above, that is, according to the definition of the energy range as the "energy of and above the Compton edge", it is permitted to neglect the energy which has been imparted to the detection element 12 by the Compton effect, namely, to acquire an energy spectrum whose principal component is a photoelectric peak involved in the occurrence of the photoelectric effect. Incidentally, this is none other than "to acquire gamma rays having imparted predetermined energy to radiation detection means" stated in the present invention.

Now, referring back to FIG. 3, when data acquisition concerning gamma rays is started, the gamma rays sensed by the detection elements 12 of the radiation detection units 1A and 1B are converted into electric signals containing their incident position information and energy information by the operations of the detection elements 12 as indicated at a step S2 in FIG. 3. Besides, the electric signals are sent to the time stamp portions 21 so as to stamp sensing times, as indicated at a step S3 in FIG. 3, and they are thereafter sent to the coordinate detection portions 22 so as to extract the position information items of the gamma rays, as indicated at a step S4 in FIG. 3.

Subsequently, at a step S5 in FIG. 3, whether or not the energy levels of the gamma rays fall within the energy range preset in the above, namely, within the "energy of and above the Compton edge" is judged in the energy discrimination portions 23. Here, on condition that the energy levels of the gamma rays are judged to fall within the energy range, whether or not the sensing times stamped in the above are equal in the respective radiation detection portions 1A and 1B, namely, whether or not the gamma rays were "coincidentally" sensed, is decided by the coincidence decision unit 3 (step S7 in FIG. 3). Further, when the gamma rays are judged to have been sensed "non-coincidentally", the data are discarded (step S81 in FIG. 3), and when they are judged to have been sensed "coincidentally", the data are sent to the data acquisition unit 4 (step S82 in FIG. 3).

On the other hand, at a step S6 in FIG. 3, regarding the electric signals coincidentally outputted from any two detection elements 12 in either the radiation detection unit 1A or 1B, whether or not the added energy value of these electric signals is equal to a "predetermined value" set beforehand is decided by the added-energy discrimination portion 25. Incidentally, the electric signals recognized as having been coincidentally outputted are selected on the basis of the sensing times stamped by the time stamp portions 21, in the coincidentality decision portions 24 before the step S6 in FIG. 3.

Here, the above "predetermined value" is set on the basis of a background as stated below, in this embodiment. First, in general, regarding the pair of gamma rays as in this embodiment, the energy spectrum thereof is obtained as one shown in FIG. 5. Depicted in the figure are a photoelectric peak P1 seen near an energy value of 511 keV which is peculiar to the gamma rays, spectra S1–S4 which are respectively observed by first–fourth Compton scatterings, a spectrum S in the case where the spectra S1–S4 are simultaneously observed, etc. Besides, a part which looks like, so to speak, a "wall" near an energy value of 340 keV is the Compton edge stated above (symbol CE in the figure) (that is, Ee max≅340 keV). By the way, it is directly seen from FIG. 5 that the gamma rays participating in the photoelectric peak P1 are chiefly acquired in the above energy discrimination portions 23.

Meanwhile, each gamma ray incident on the detection element 12 undergoes the interactions, such as photoelectric effect and Compton effect, with this detection element 12 as stated above. In this embodiment, among the gamma rays, the gamma ray which causes the photoelectric effect after having undergone the Compton scattering once is especially noted. Regarding such a gamma ray, a case is considered where, as shown in FIG. 6 by way of example, it undergoes the Compton scattering in a certain detection element 121 on the radiation detection unit 1A or 1B and thereafter causes the photoelectric effect in "another" detection element 122.

Besides, in such a case, energy Ee below the Compton edge CE is imparted to the detection element 121, and energy involved in the photoelectric effect is imparted to the other detection element 122 by a scattered gamma ray Gs (refer to FIG. 6) which has been deprived of the energy Ee.

Figure 6:
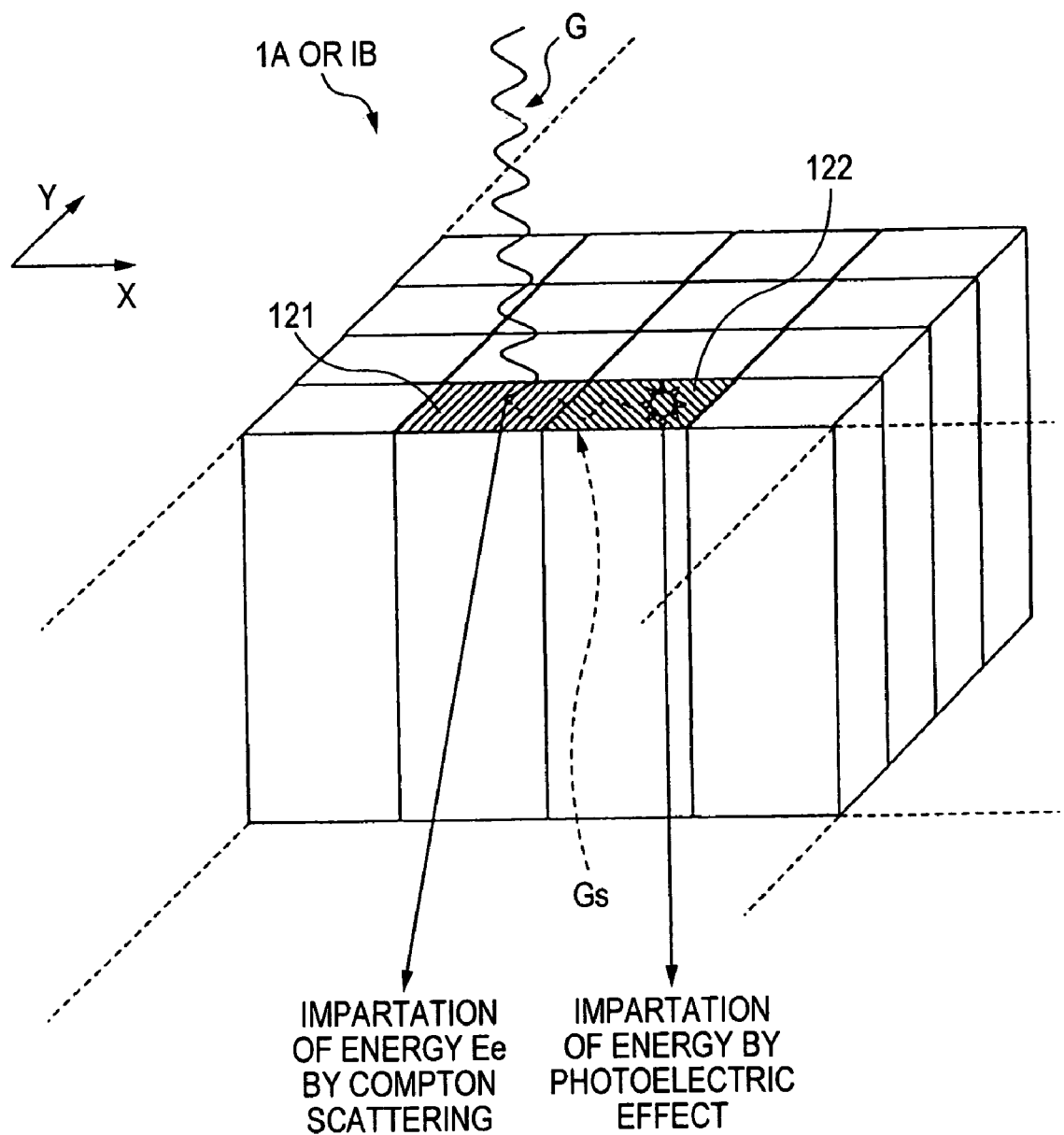
FIG. 6 is an explanatory diagram for explaining a case where a gamma ray gives rise to a photoelectric effect after having undergone Compton scattering once, in a radiation detection unit.

Accordingly, assuming now that the Compton scattering in the detection element 121 as shown in FIG. 6 be backward scattering, an energy value obtained by the subtraction of about 340 keV being the energy value of the Compton edge CE, from about 511 keV being the energy value of the gamma ray G, that is, energy "near 171 keV" is observed in the other detection element 122.

Figure 5:
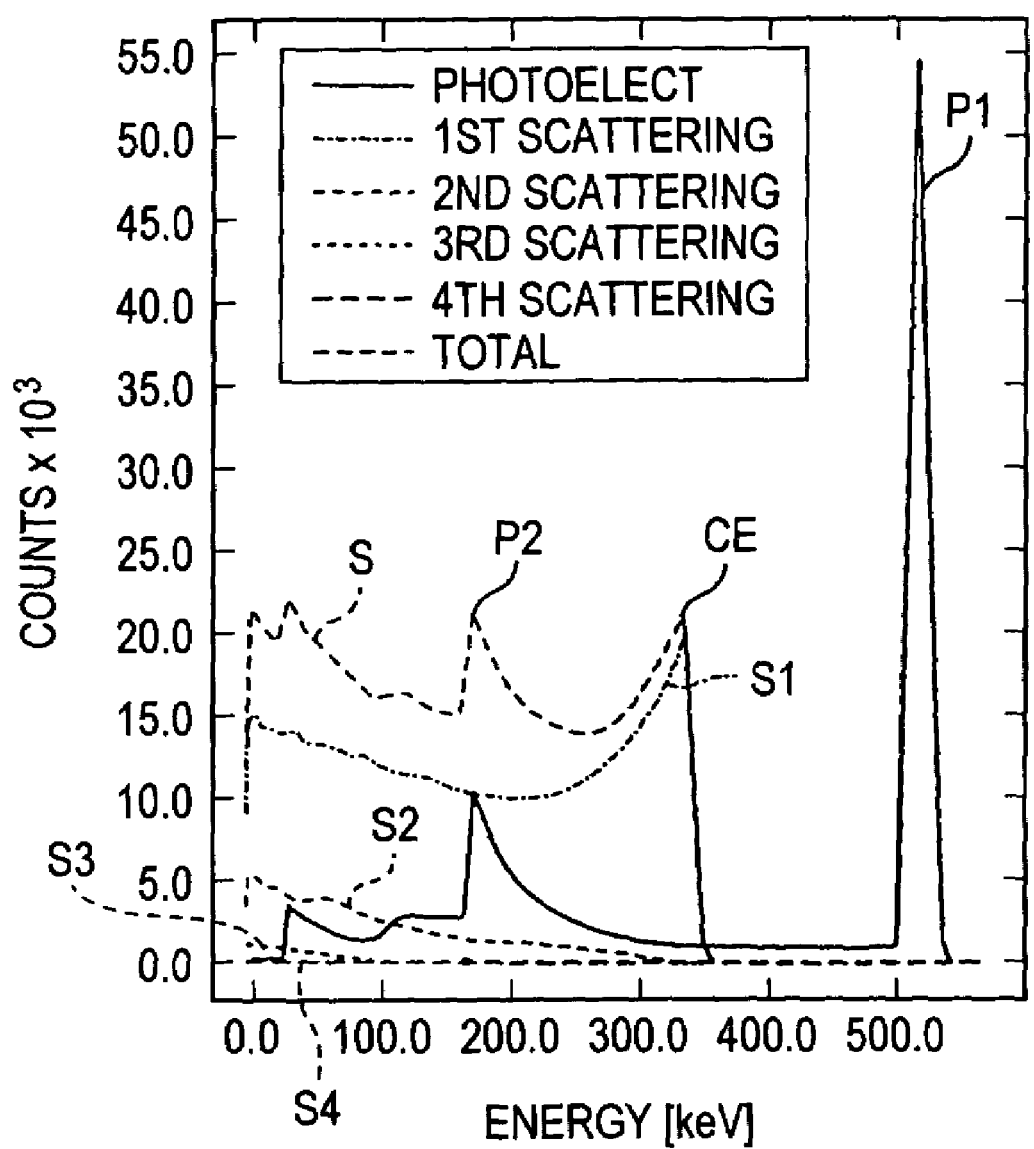
FIG. 5 is a graph showing the energy spectra of a pair of gamma rays, wherein the axis of abscissas represents the value of energy, while the axis of ordinates represents the number of counts (a count value).

These facts result in the following: If the added value of the energy information items observed at any two detection elements 12 in either the radiation detection unit 1A or 1B is near 511 keV (and besides, the energy information is near 171 keV in one of the detection elements), the existence of the detection element 121 and the other detection element 122 as stated above is presumed. In other words, the existence of the gamma ray which has caused the photoelectric effect after having undergone the Compton scattering once is presumed. That is, the "predetermined value" stated above signifies "near 511 keV", and even the gamma ray participating in such a behavior is set as a subject for the acquisition in order to form the basis of imaging in this embodiment. Incidentally, it is indicated in FIG. 5 that a peak P2 near 171 keV is certainly observed.

Incidentally, as explained with reference to FIG. 4, the Compton edge CE is the maximum energy (=Ee max) which is lost (=which is imparted to the electron E) in the case where the gamma ray G undergoes the Compton scattering. Therefore, whatever Compton scattering phenomenon has occurred, an energy value at which the peak P2 as shown in FIG. 5 will be observed cannot become below near 171 (=511–"near 340") keV. The word "near" in "near 171 keV" stated now can define an approximately appropriate range on the basis of the above circumstances. Incidentally, regarding the word "near", reference should be had also to later description.

Besides, in such a case, the electric signals are "coincidentally" detected from the two detection elements 12 (the detection elements 121 and 122 in FIG. 6), so that the incident position of the pertinent gamma ray in the radiation detection unit 1A or 1B is specified as stated below. Energy values (=imparted energy quantities) observed in the two detection elements 12 are confirmed, whereupon that one of the detection elements 12 as to which the peak P2 was "not observed", namely, the detection element 12 as to which an energy value near the Compton edge CE was observed (in FIG. 6, the detection element 121) may be specified as the incident position. Incidentally, for this purpose, positional coordinate data concerning the two detection elements 12 is transmitted from the coordinate detection portion 22 to the added-energy discrimination portion 25 as shown in FIG. 3, and the incident position (coordinates) is specified in the discrimination portion 25 on the basis of the data and the above idea.

The arithmetic operation as explained above is executed at the step S6 in FIG. 3, or in the added-energy discrimination portion 25 in FIG. 2. Besides, the data thus discriminated is delivered to the coincidence decision unit 2, likewise to the data passed through the energy discrimination portion 23, and whether or not the corresponding gamma rays were "coincidentally" detected (=coincidence) in each of the radiation detection units 1A and 1B (at step S7 in FIG. 3). The data transmission to the data acquisition unit 4 (step S82 in FIG. 3) or the data discard (step S81 in FIG. 3) is executed on the basis of the decision.

After all, in this embodiment, even the gamma rays which have caused the photoelectric effect after having undergone the Compton scattering once in either or both of the radiation detection units 1A and 1B can be set as subjects for the acquisition. More concretely, in this embodiment, coincidence acquisitions conforming to the following three patterns are carried out:

The first pattern is that gamma rays caused a photoelectric effect in the radiation detection unit 1A (or 1B) and caused a photoelectric effect "also" in the radiation detection unit 1B (or 1A), and they were coincidentally detected. The second pattern is that gamma rays caused a photoelectric effect in the radiation detection unit 1A (or 1B) after having undergone Compton scattering once and caused a photoelectric effect "also" in the radiation detection unit 1B (or 1A) after having undergone Compton scattering once, and they were coincidentally detected. The third pattern is that gamma rays caused a photoelectric effect in the radiation detection unit 1A or 1B and caused a photoelectric effect in the radiation detection unit 1B or 1A after having undergone Compton scattering once, and they were coincidentally detected.

Incidentally, it has been described above that the predetermined value is set "near 511 keV", and that the discrimination in the added-energy discrimination portion 25 is based on whether or not the added value of the energy information outputs coincidentally delivered from the two detection elements 12 agrees with the predetermined value. However, it is more actual and more practicable to endow the predetermined "value" with a certain degree of width.

By way of example, it is possible to pass the signal through the added-energy discrimination portion 25 in a case where energy "166 keV to 350 keV" is observed in one of the two detection elements 12, while energy "330 keV to 526 keV" is observed in the other. That is, in this case, the predetermined value stated above has a width of "496–876 keV", and the signal is passed through the added-energy discrimination portion 25 when the added value of the observed energy information items lies within the range of the width. Incidentally, it is needless to say that, in the example stated now, the latter in which the energy value of "330 keV to 526 keV" is observed is the detection element which caused the Compton scattering, while the former in which the energy of "166 keV to 350 keV" is observed is the detection element which caused the photoelectric effect after the Compton scattering. By the way, such circumstances are also contained in the concept "near" stated above to some extent.

Thereafter, the gamma-ray acquisition as stated above is continued till the completion thereof (step S9 in FIG. 3). Whether or not the acquisition has been completed, is determined by referring to the time period for the acquisition or the number of counts for the acquisition as set beforehand. Besides, the acquisition can be sometimes ended midway in compliance with a direct command given by the user of the apparatus.

As thus far described, according to the nuclear medical diagnosis apparatus in this embodiment, only the gamma rays which caused merely the photoelectric effect are not set as subjects for acquisition, but the gamma rays which caused the photoelectric effect after having undergone the Compton scattering once are also set as subjects for acquisition, so that an acquisition efficiency for the gamma rays of high energy can be enhanced. Besides, this advantage can be remarkably enjoyed especially in the radiation detection unit 1A or 1B whose stopping power is comparatively low. Owing to these facts, in this embodiment, image creation can be performed on the basis of more information items, so that an image of higher precision and higher quality can be obtained.

Incidentally, it has been described in this embodiment that, in the case where the gamma rays which caused the photoelectric effect after the Compton scattering are to be acquired, the added-energy discrimination portion 25 executes the arithmetic operations concerning the discrimination as to "any" detection elements 12. The present invention, however, can be performed in an aspect where the operations are executed as to "adjacent" detection elements 12. For this purpose, an example of construction in which an adjacency decision portion 2N is added as exemplified in FIG. 7 may be adopted instead of the construction of the gamma-ray energy discrimination unit 2A or 2B shown in FIG. 2. Besides, position information is necessary for deciding whether or not the detection elements are "adjacent". It is therefore indicated that the adjacency decision portion 2N in FIG. 7 receives an output from the coordinate detection portion 22.

Incidentally, the word "adjacent" stated here is a term intended to signify the relationship between a certain noticed one 12 of detection elements 12 which are arrayed, for example, in the shape of a two-dimensional matrix and the eight detection elements 12 which exist around the noticed detection element 12 (of course, when the detection element 12 arrayed at the peripheral edge or corner of the matrix is noticed, the word "adjacent" signifies the relationship of the noticed detection element 12 and the five or three detection elements 12).

In this way, arithmetic operations tacitly premised in the above embodiment as sweep the whole area of the radiation detection unit 1A or 1B are dispensed with, so that an arithmetic speed can be enhanced. By the way, in view of the fact that most of the gamma ray which cause the photoelectric effect after having undergone the Compton scattering once, usually give rise to the pertinent phenomenon between the adjacent detection elements 121 and 122 a shown in FIG. 6, such restriction of the detection elements for the arithmetic operations as stated above does not pose any serious problem (for example, that an acquisition efficiency lowers drastically) in actuality.

Figure 7:
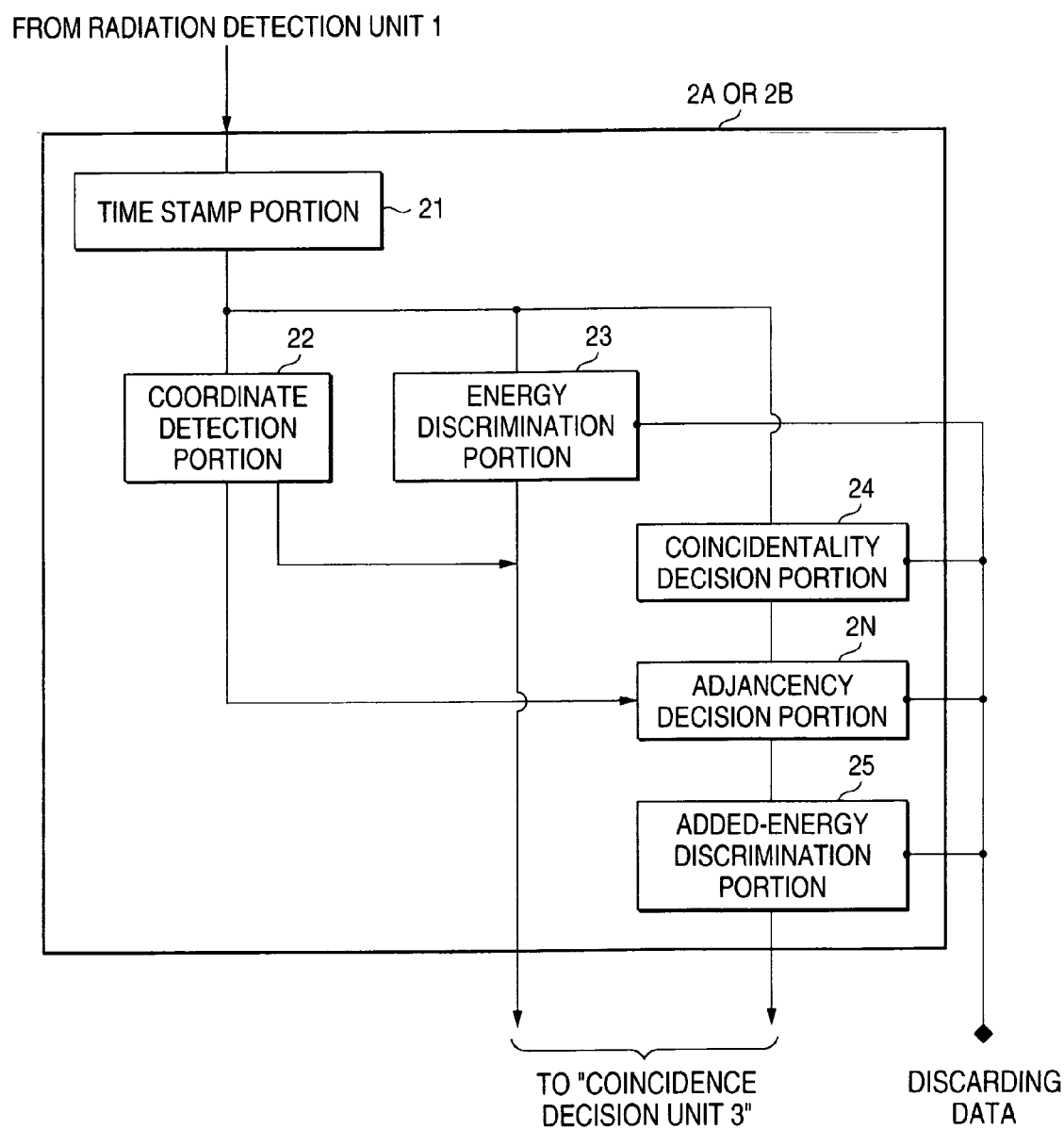
FIG. 7 is an outline diagram showing an example of construction of a gamma-ray energy discrimination unit which is different from the unit shown in FIG. 2.
Figure 8:
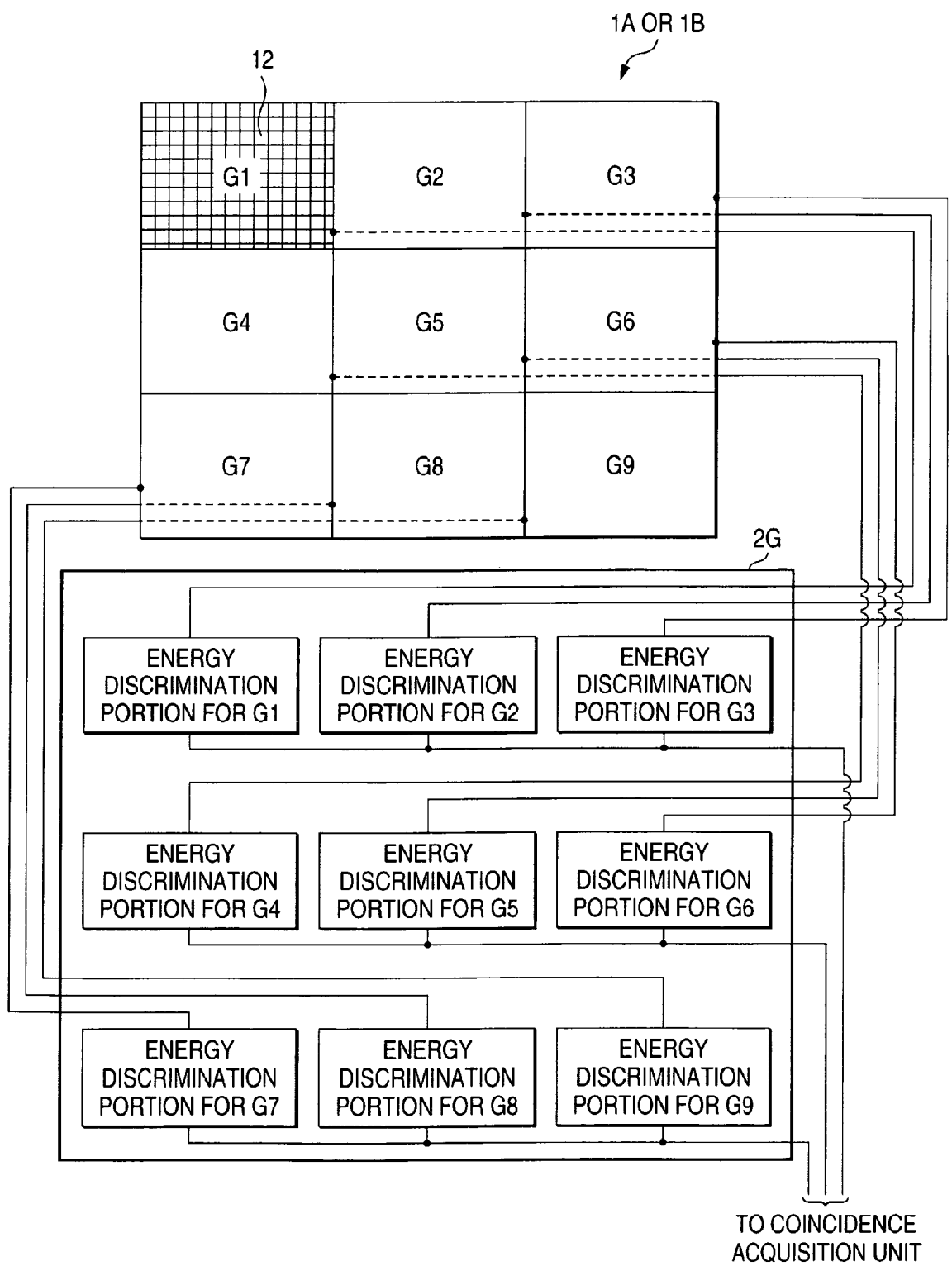
FIG. 8 is an outline diagram showing an example of construction in which detection elements in each radiation detection unit are divided into a plurality of groups, and which has an energy discrimination portion every group.

Besides, from the viewpoint of enhancing an arithmetic speed, it is favorable to adopt an aspect in which the detection elements 12 on the radiation detection units 1A and 1B in the above embodiment are divided into a plurality of groups G1, . . . , G9 as shown in FIG. 8 by way of example, and an energy discrimination unit 2G capable of executing arithmetic operations in units of the groups G1, . . . , G9 is included, whereby the arithmetic operations for added-energy discriminations are executed in parallel. By the way, in FIG. 8, each block in the energy discrimination unit 2G has the same construction as shown in FIG. 2 or FIG. 7. In this way, each of the blocks may render the coincidentality decision for the two detection elements 12 as shown in FIG. 6 by way of example, as to only the corresponding one of the groups G1, . . . , G9, so that the arithmetic speed can be enhanced for the same reason as stated above. Incidentally, since the number of groups need not always be set at "9" in the present invention, it may, of course, be set at will.

Further, in the above embodiment, the so-called "semiconductor detectors" utilizing the semiconductor detection elements have been explained as the radiation detection units 1A and 1B. Of course, however, the present invention is not restricted to such an aspect, but it is similarly applicable to, for example, a case of utilizing a scintillation camera whose scintillator is made of NaI, BGO, LSO or the like. Even in such a case, the advantage of enhancing an acquisition efficiency for gamma rays of high energy is similarly enjoyed. Incidentally, on this occasion, especially in a case where the scintillator is made of NaI, the stopping power thereof is said to be comparatively low, and hence, the application of the present invention is more advantageous.

Figure 9:
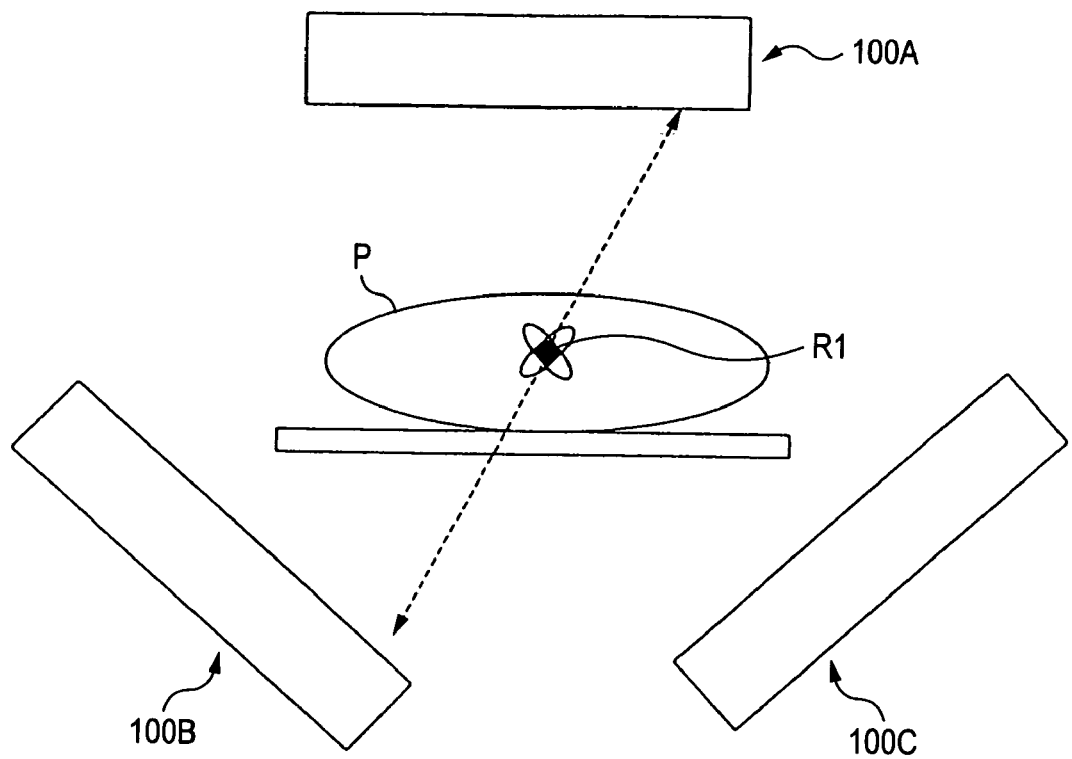
FIG. 9 is an outline diagram showing an example of construction in the case where three radiation detection units are disposed.

Still further, the nuclear medical diagnosis apparatus according to the present invention is not restricted to the above example of construction as shown in FIG. 1 and FIG. 2, FIG. 7 or FIG. 8 or the above processing flow shown in FIG. 3. By way of example, in the foregoing, the two radiation detection units 1 (1A and 1B) are disposed, and they are arranged so as to oppose to each other with the subject P interposed therebetween. In some cases, however, it is allowed to adopt an aspect in which three radiation detection units 100A, 100B and 100C are disposed as shown in FIG. 9, or in which three or more radiation detection units 1 are disposed. In such a case, for example, in the case of FIG. 9, coincidence decisions (acquisitions) may be done between the radiation detection units 100A and 100B, 100B and 100C, and 100C and 100A.

Besides, the above aspect in FIG. 3 is such that the gamma-ray acquisition and the coincidence decision are done, so to speak, in parallel. It is also allowed, however, to adopt instead of the aspect, a construction or a processing flow in which, after gamma rays have been entirely acquired once on the basis of a predetermined acquisition time period or acquisition count number, all the data thereof are collectively submitted to coincidence decisions.

As described above, according to the nuclear medical diagnosis apparatus of the present invention, gamma rays which cause a photoelectric effect after having undergone Compton scattering once are also set as subjects for acquisition, whereby an acquisition efficiency for the gamma rays of high energy can be enhanced in a radiation detection unit. This advantage becomes remarkable especially in a case where a semiconductor detector of comparatively low stopping power is utilized as the radiation detection unit. Besides, as a result, an image to be created becomes preciser, and its image quality can be enhanced.

What is claimed is:

1. A nuclear medical diagnosis apparatus comprising:
   first and second radiation detectors configured to detect gamma rays emitted from a radioisotope in a subject and output electric signals;
   a first energy discrimination unit configured to individually discriminate the electric signals output from the first radiation detector, on the basis of energy;
   a first coincidence determination unit configured to determine a pair of electric signals which are included among the electric signals output from the first radiation detector and which have undergone Compton scattering, on the basis of coincidence of the gamma rays that are incident on the first radiation detector;
   a first addition/energy discrimination unit configured to add the pair of the electric signals determined by the first coincidence determination unit and individually discriminate resultant electric signals on the basis of energy;
   a second energy discrimination unit configured to individually discriminate the electric signals output from the second radiation detector, on the basis of energy;
   a second coincidence determination unit configured to determine a pair of electric signals which are included among the electric signals output from the second radiation detector and which have undergone Compton scattering, on the basis of coincidence of the gamma rays that are incident on the second radiation detector;
   a second addition/energy discrimination unit configured to add the pair of the electric signals determined by the second coincidence determination unit and individually discriminate resultant electric signals on the basis of energy;

a third coincidence determination unit configured to determine coincidence between the gamma rays incident on the first radiation detector and the gamma rays incident on the second radiation detector, on the basis of outputs from the first energy discrimination unit, outputs from the first addition/energy discrimination unit, outputs from the second energy determination unit and outputs from the second addition/energy discrimination unit; and an image generation unit configured to generate an image representing spatial distribution of the radioisotope, on the basis of determination results obtained by the third coincidence determination unit.

2. The nuclear medical diagnosis apparatus according to claim 1, wherein each of the first and second radiation detectors is a semiconductor detector.

* * * * *